US012661435B2

(12) United States Patent
Akagi et al.

(10) Patent No.: US 12,661,435 B2
(45) Date of Patent: Jun. 23, 2026

(54) MEDICAL INSTRUMENT

(71) Applicant: THE UNIVERSITY OF TOKYO, Tokyo (JP)

(72) Inventors: Yuki Akagi, Tokyo (JP); Yasutaka Anraku, Tokyo (JP); Ichiro Sakuma, Tokyo (JP); Hayato Laurence Mizuno, Tokyo (JP)

(73) Assignee: THE UNIVERSITY OF TOKYO, Tokyo (JP)

( * ) Notice: Subject to any disclaimer, the term of this patent is extended or adjusted under 35 U.S.C. 154(b) by 1201 days.

(21) Appl. No.: 17/625,385

(22) PCT Filed: Jul. 9, 2020

(86) PCT No.: PCT/JP2020/026910
§ 371 (c)(1),
(2) Date: Apr. 28, 2022

(87) PCT Pub. No.: WO2021/006318
PCT Pub. Date: Jan. 14, 2021

(65) Prior Publication Data

US 2022/0387674 A1 Dec. 8, 2022

Related U.S. Application Data

(60) Provisional application No. 62/872,911, filed on Jul. 11, 2019.

(51) Int. Cl.
*A61L 29/16* (2006.01)
*A61L 29/08* (2006.01)

(52) U.S. Cl.
CPC ............ *A61L 29/16* (2013.01); *A61L 29/085* (2013.01); *A61L 2300/602* (2013.01); *A61L 2400/12* (2013.01)

(58) Field of Classification Search
CPC .. A61L 29/16; A61L 29/085; A61L 2300/602; A61L 2400/12; A61L 2300/204;
(Continued)

(56) References Cited

U.S. PATENT DOCUMENTS

| | | | | |
|---|---|---|---|---|
| 9,259,398 | B1 * | 2/2016 | Klein | A61K 47/183 |
| 2001/0000510 | A1 | 4/2001 | Sakurai et al. | |

(Continued)

FOREIGN PATENT DOCUMENTS

| | | | |
|---|---|---|---|
| JP | 8-188541 | A | 7/1998 |
| JP | 2001-131271 | A | 5/2001 |

(Continued)

OTHER PUBLICATIONS

Japanese Office Action for corresponding Japanese Application No. 2021-530730, dated Mar. 5, 2024, with English translation.

(Continued)

*Primary Examiner* — Jeffrey T. Palenik
(74) *Attorney, Agent, or Firm* — Birch, Stewart, Kolasch & Birch, LLP

(57) ABSTRACT

In a medical instrument that is inserted into an affected area or tissue to perform treatment, a technique of delivering various drugs to a target site is desired.

Provided is a medical instrument that is inserted into an affected area or tissue to perform treatment, wherein a drug-loaded nanostructure is covalently bound to the medical instrument via a photosensitive linker immobilized on the surface of at least a portion of the medical instrument.

16 Claims, 5 Drawing Sheets

(B)

(58) Field of Classification Search
CPC ......... A61L 2300/624; A61L 2300/626; A61L 31/10; A61L 31/16; A61K 9/0009; A61B 17/12136; A61B 2017/00893; A61B 2017/00942; A61F 2250/0067; A61M 2025/0057; A61M 2025/105
See application file for complete search history.

(56) References Cited

U.S. PATENT DOCUMENTS

| | | | |
|---|---|---|---|
| 2002/0082198 A1 | 6/2002 | Sakurai et al. | |
| 2006/0025330 A1 | 2/2006 | Sakurai et al. | |
| 2006/0100568 A1 | 5/2006 | Tan | |
| 2009/0157042 A1 | 6/2009 | Cheng et al. | |
| 2014/0276356 A1 | 9/2014 | Victor et al. | |
| 2014/0358122 A1 | 12/2014 | Yamashita et al. | |
| 2017/0196990 A1 * | 7/2017 | Johnson | A61K 47/68 |

FOREIGN PATENT DOCUMENTS

| | | | |
|---|---|---|---|
| JP | 2007-23023 | A | 2/2007 |
| JP | 2008-507336 | A | 3/2008 |
| JP | 2011-505984 | A | 3/2011 |
| JP | 2012-519540 | A | 8/2012 |
| JP | 2016-512151 | A | 4/2016 |
| WO | WO 01/32230 | A2 | 5/2001 |
| WO | WO 2010/101722 | A2 | 9/2010 |
| WO | WO 2014/152823 | A1 | 9/2014 |
| WO | WO 2014/163091 | A1 | 10/2014 |

OTHER PUBLICATIONS

International Search Report for International Application No. PCT/JP2020/026910, dated Oct. 6, 2020, with English translation.
Japanese Notice of Allowance for Japanese Application No. 2021-530730, dated Mar. 4, 2025, with an English translation.
Japanese Office Action for Japanese Application No. 2021-530730, dated Jul. 30, 2024, with an English translation.

* cited by examiner

[Figure 1]
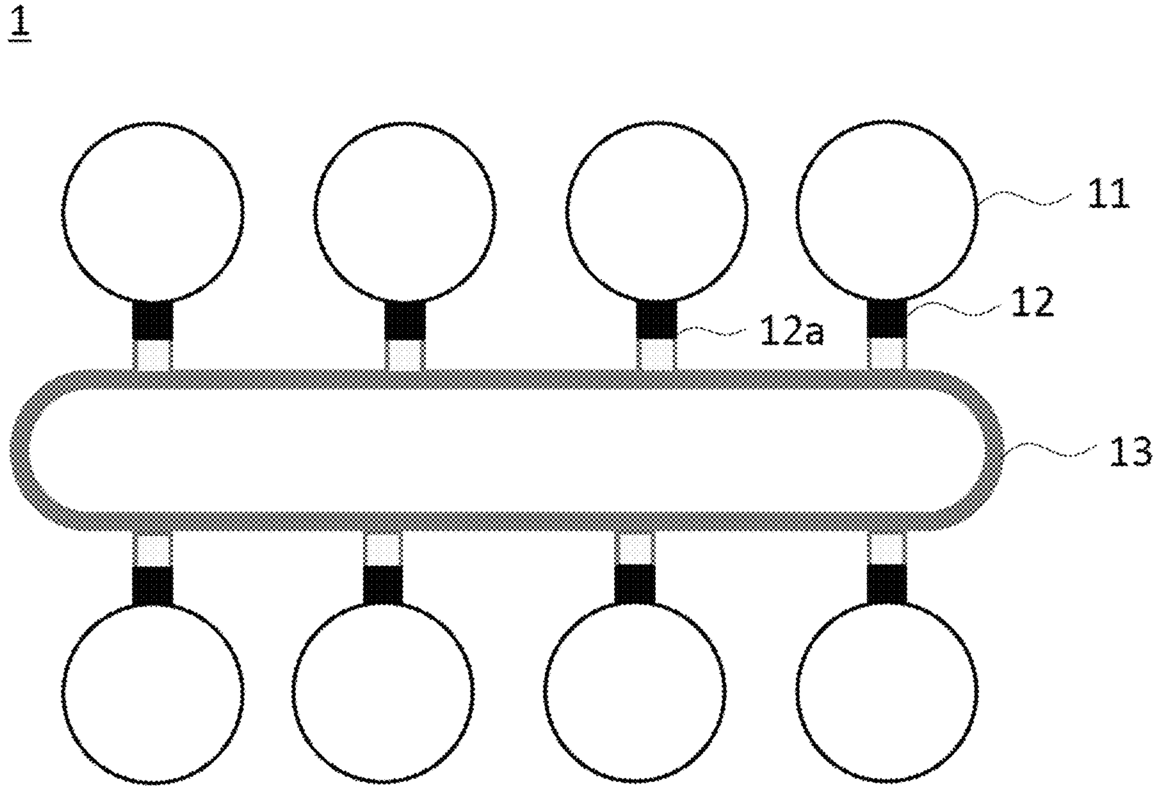
[Figure 2]
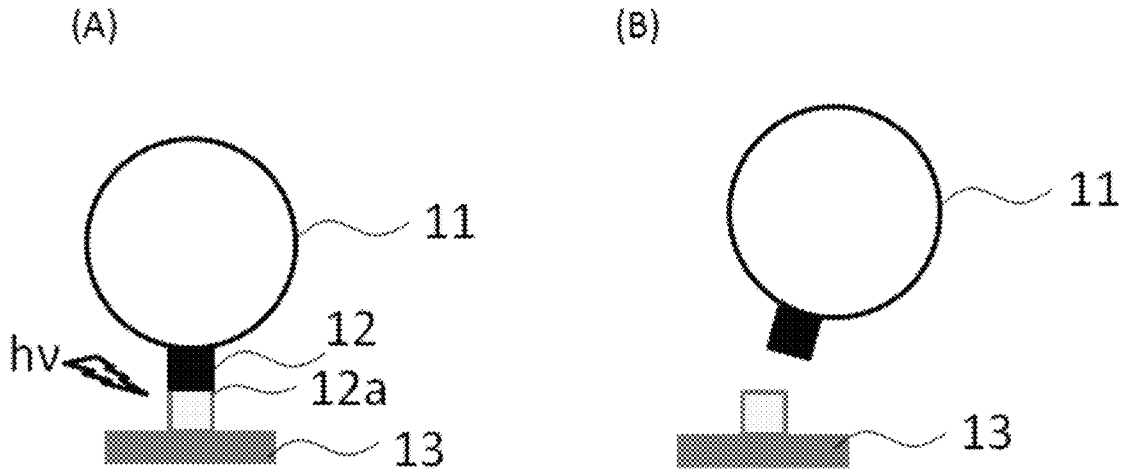

[Figure 3A]
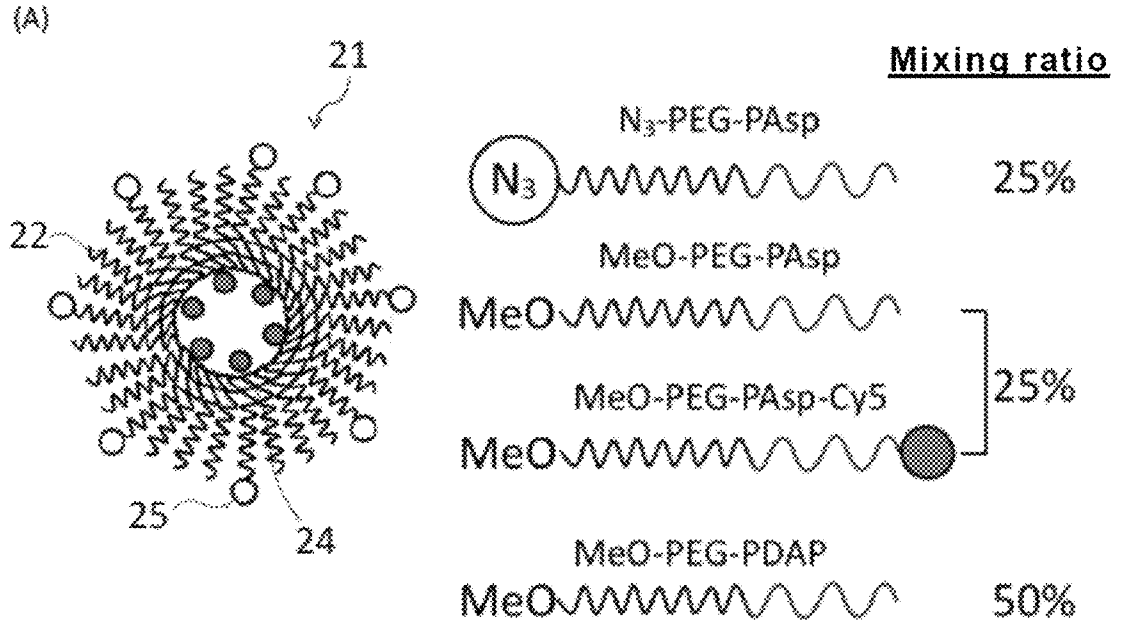
[Figure 3B]
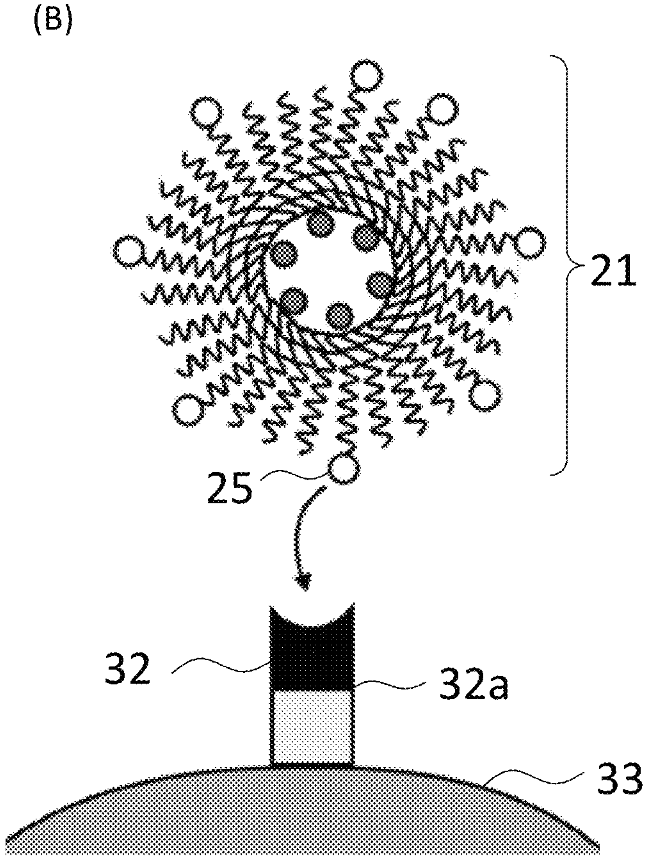

[Figure 3C]
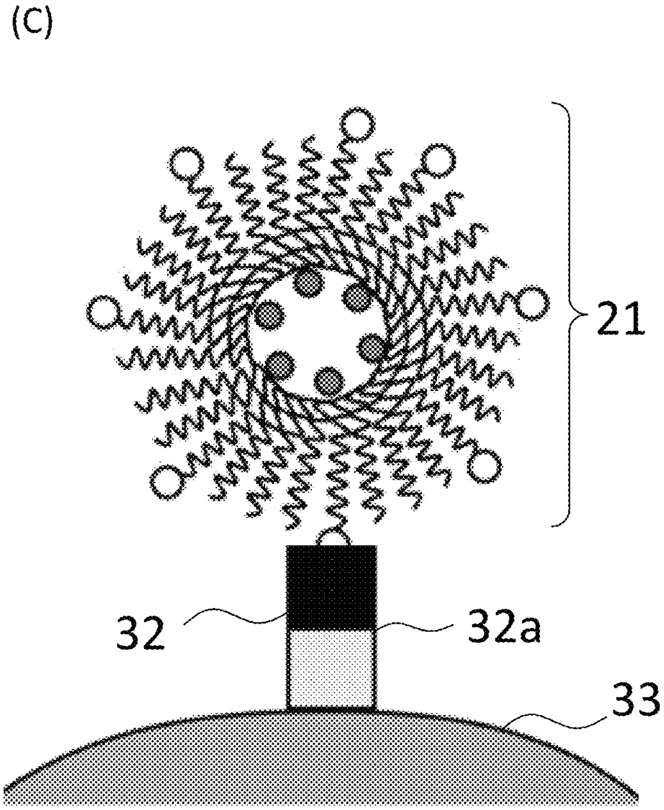
[Figure 3D]
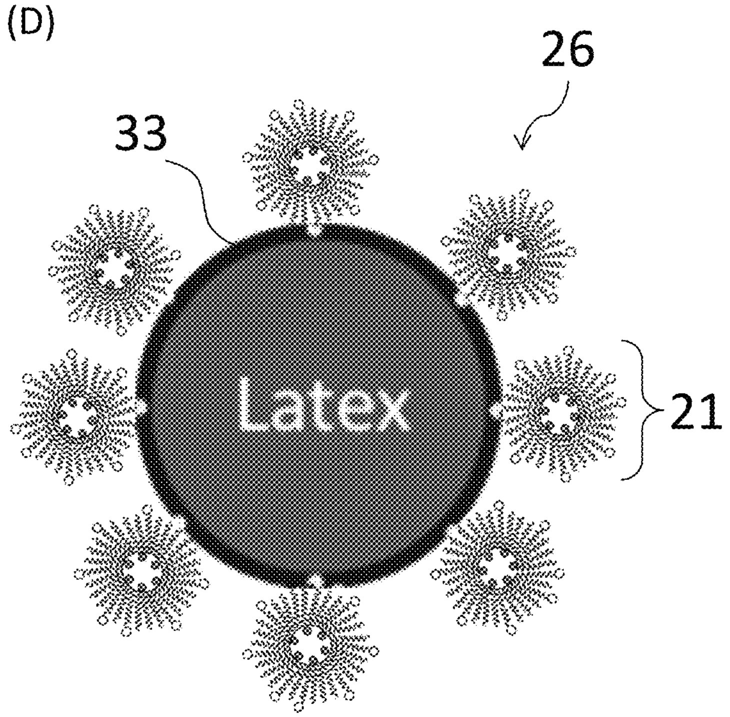

[Figure 4]
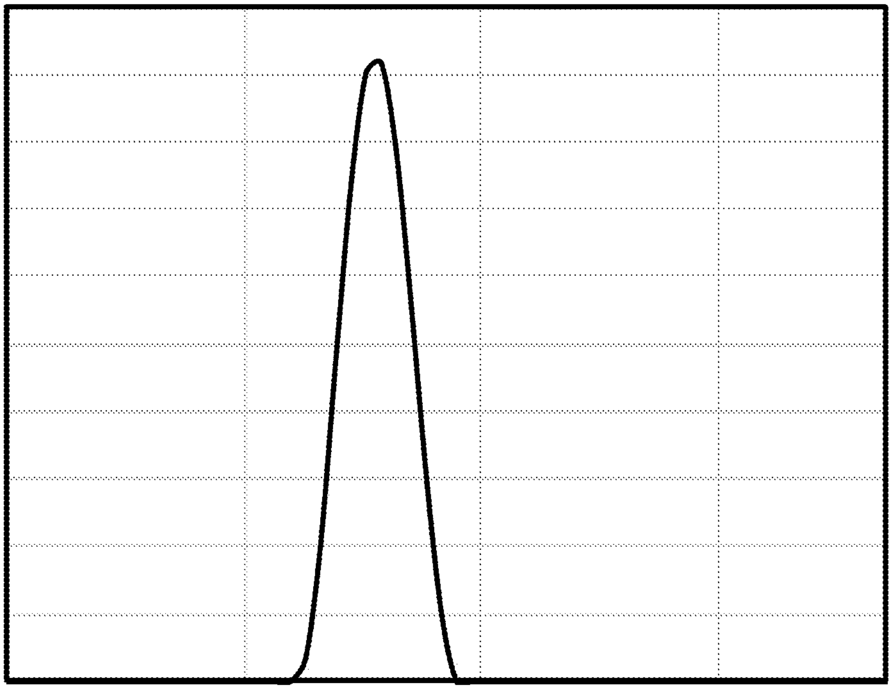
[Figure 5]
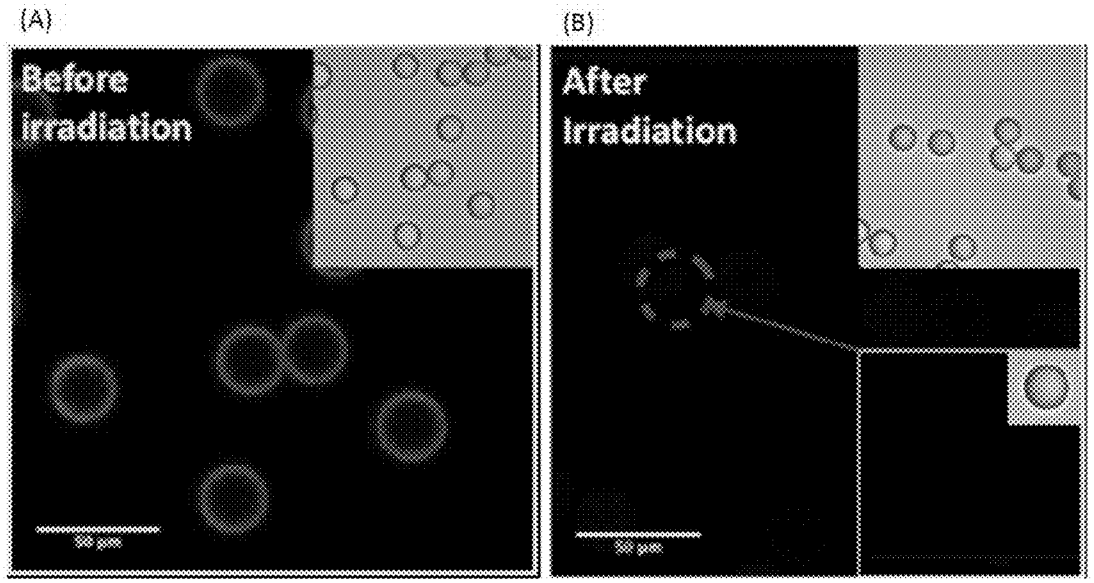

[Figure 6]
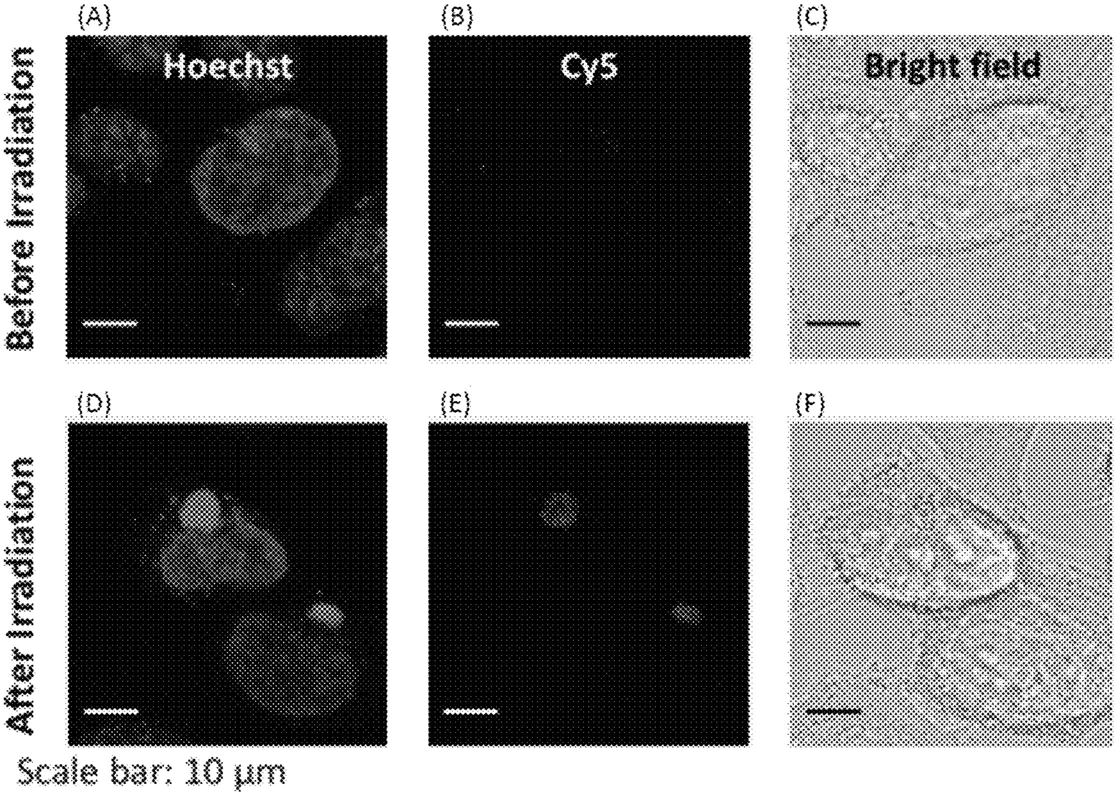

MEDICAL INSTRUMENT

CROSS REFERENCE TO RELATED APPLICATIONS

This application is the National Phase of PCT International Application No. PCT/JP2020/026910, filed on Jul. 9, 2020, which claims priority under 35 U.S.C. 119(e) to U.S. Provisional Application No. 62/872,911, filed on Jul. 11, 2019, all of which are hereby expressly incorporated by reference into the present application.

TECHNICAL FIELD

The present invention relates to a medical instrument that is inserted into an affected area or tissue to perform treatment. More specifically, the present invention relates to a medical instrument capable of releasing a substance such as a drug in a targeted affected area or tissue.

BACKGROUND ART

Various diseases have been generally treated by inserting a medical instrument into an organism lumen such as blood vessel, esophagus, airway, sinus, trachea, colon, bile duct, urinary tract, prostate or intracerebral duct. For example, a medical instrument such as a stent, a catheter or a balloon catheter has been used for the treatment of vascular diseases.

Among others, percutaneous transluminal coronary angioplasty (PTCA) is one of treatments for coronary artery diseases. PTCA is a method which comprises allowing a medical balloon to reach a narrowed site through a blood vessel, and then inflating the balloon to dilate the stenosis. When compared with surgical operation or drug therapy, PTCA is considered to be a minimally invasive and fast-acting treatment method. PTCA is broadly divided into two types of treatments, depending on whether only the inflation of the balloon is carried out or a stent is placed as well as the inflation of the balloon upon the dilatation of the stenosis. It has been known that the former PTCA has a risk of restenosis, whereas the latter PTCA has a risk of thrombus formation. In recent years, directed towards achieving the treatment of stenosis only with a balloon, which does not leave foreign matters in a body and causes only a small risk of thrombus formation, a drug eluting balloon (DEB) that suppresses a risk of restenosis has been developed. The balloon surface of DEB is coated with a drug that suppresses cell proliferation. According to DEB, a balloon is allowed to come into contact with a narrowed site upon the inflation of the balloon, so that a drug coated on the outer surface of the balloon can be administered to the affected area, and thereby, restenosis can be suppressed. However, at present, in the case of clinically used DEB, since the drug is only applied onto the surface of the balloon, the drug is easily dissociated, and the drug is gradually removed due to blood flow from the time point at which the balloon is inserted into the blood vessel. It has been known that, as a result, 6% to 7% of the drug is dissociated from the balloon surface before the balloon reaches the affected area. In addition, even after the balloon has inflated, 10% to 20% of the drug remains on the surface of the balloon. Consequently, the amount of the drug that is actually incorporated into cells is 50% to 60% of the amount of the initially applied drug, and thus, the outflowing of a large amount of drug into the blood, as well as low drug delivery efficiency, has been problematic (Patent Literature 1: International Publication No. WO2014/163091). Moreover, in the first place, some drugs cannot be applied onto the surface of such a balloon, and thus, DEB is also problematic in terms of limitation of applicable drugs. Furthermore, in the case of the existing DEBs, a large amount of drug loaded on the DEB is dissociated before the DEB reaches a target site, and further, it is difficult to control the drug remaining on the balloon after completion of dilatation/modification. Hence, it is necessary to administer the drug to the affected area by a single balloon dilatation. However, the amount of drug that can be released by such a single balloon dilatation is also restricted by the period of time in which the blood flow can be suspended (possibly, 0.5 to 1.0 min), and thus, it is difficult to increase the amount of the drug to be delivered to a target site.

The control of drug release from the coating layer of a medical instrument such as DEB has also been studied. For example, Patent Literature 2 (International Publication No. WO2014/152823) discloses a medical instrument comprising a coating modified with a photosensitive linker that is covalently bound to a reagent. Patent Literature 2 describes that a photosensitive bond is cleaved by exposing the coating to a light, and that the reagent is released to a site closest to the cleaved site. However, in the case of this medical instrument, since the functional group of the reagent itself is covalently bound to the photosensitive linker, the medical instrument is problematic in that the function or activity of the reagent may be impaired, or in that the type of a covalently bound reagent is limited.

CITATION LIST

Patent Literature

Patent Literature 1: International Publication No. WO2014/163091
Patent Literature 2: International Publication No. WO2014/152823

SUMMARY OF INVENTION

Under the aforementioned circumstances, it has been still desired to develop a technique of delivering various drugs to a target site in a medical instrument that is inserted into an affected area or tissue to perform treatment.

The present invention is, for example, as follows.

[1] A medical instrument that is inserted into an affected area or tissue to perform treatment, wherein a drug-loaded nanostructure is covalently bound to the medical instrument via a photosensitive linker immobilized on the surface of at least a portion of the medical instrument.

[2] The medical instrument according to the above [1], wherein the size of the nanostructure is 20 nm to 500 nm.

[3] The medical instrument according to the above [1] or [2], wherein the nanostructure is at least one selected from among a micelle, a polymeric micelle, a liposome, a polymersome, a nanogel, a nanoparticle, a nanorod, and a nanosphere.

[4] The medical instrument according to any one of the above [1] to [3], wherein the drug comprises at least one selected from among an agent, a pharmaceutical product, a diagnostic drug, and a nutritional supplement.

[5] The medical instrument according to any one of the above [1] to [4], wherein the drug is enclosed in the nanostructure, or is physically or chemically bound to the nano structure.

[6] The medical instrument according to any one of the above [1] to [5], wherein the drug is soluble or insoluble in water.

[7] The medical instrument according to any one of the above [1] to [6], wherein the photosensitive linker is cleaved or decomposed by being exposed to a light, so that the nanostructure is released.

[8] The medical instrument according to the above [7], comprising two or more types of photosensitive linkers that are cleaved or decomposed with light each having different wavelengths.

[9] The medical instrument according to any one of the above [1] to [8], wherein the photosensitive linker comprises at least one selected from among a double bond that binds two carbon atoms to each other, an azo bond, a peroxide bond, a bond that binds a carbon atom to a nitrogen atom, and a structure represented by the following formula [I]:

(I)

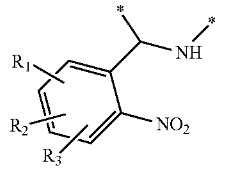

wherein * represents a binding site, and $R_1$, $R_2$, and $R_3$ each independently represent a hydrogen atom, lower alkyl, lower alkoxy, amino, a halogen atom (F, Cl, Br, or I), hydroxy or cyano, or any two of the adjacent $R_1$, $R_2$, and $R_3$ together form a methylenedioxy group.

[10] The medical instrument according to any one of the above [1] to [9], which is for use in the delivery of the drug to a tissue.

[11] The medical instrument according to any one of the above [1] to [10], wherein the tissue comprises at least one selected from among coronary vascular system, peripheral vascular system, cerebrovascular system, esophagus, airway, sinus, trachea, colon, bile duct, urinary tract, prostate, intracerebral duct, and lower limbs.

[12] The medical instrument according to any one of the above [1] to [11], which is selected from among a balloon, a catheter, a stent, and a probe.

[13] The medical instrument according to any one of the above [1] to [12], further comprising a light source for use in the exposure of the photosensitive linker to a light, wherein the light source is selected from a light-emitting diode and a semiconductor laser.

[14] The medical instrument according to any one of the above [1] to [13], further comprising a secondary medical instrument having an optical fiber or a photonic crystal fiber for use in the exposure of the photosensitive linker to a light.

[15] The medical instrument according to any one of the above [1] to [14], wherein the photosensitive linker is cleaved or decomposed by being exposed to a light in a region at a wavelength of 200 to 1000 nm.

The medical instrument of the present invention has one or more of the following effects.

(1) In the case of the medical instrument of the present invention, since a drug is delivered to a target site in a state in which the drug is loaded on a nanostructure, the present medical instrument can be applied to a variety of drugs. For example, a variety of drugs, such as a low molecular weight compound, a polymeric pharmaceutical drug, a hydrophobic substance, a hydrophilic substance, a poorly soluble substance, and a water-soluble substance, can be loaded in the present medical instrument. Moreover, since the drug itself does not need to be immobilized (covalently bound) on the medical instrument, a reduction in the function or activity of the drug due to loading or delivery can be suppressed.

(2) In the case of the medical instrument of the present invention, since the nanostructure is immobilized on the surface of the medical instrument, dissociation (leaving or falling) of the drug is suppressed or prevented in the process of delivering the drug to a target site, and thus, it is possible to stably deliver the drug to the target site. Accordingly, the medical instrument of the present invention enables efficient transportation of the drug to the target site.

(3) In the case of the medical instrument of the present invention, a photosensitive linker is cleaved or decomposed by being exposed to light, and thus, a nanostructure and/or a drug loaded on the nanostructure can be released in the target site.

In a preferred embodiment, the release behavior (speed, timing, etc.) of a nanostructure and/or a drug loaded on the nanostructure can be regulated by adjusting the amount of light exposed or the wavelength of the light.

In particular, in the case of the medical instrument of the present invention, a nanostructure and/or a drug loaded on the nanostructure are released only during light irradiation, and further, stepwise release of the drug becomes possible by adjusting the amount of a light exposed or the wavelength of the light. The drug is released multiple times by repeating light irradiation (for example, the stopping of the blood flow (possibly, for 0.5 to 1.0 min) is repeated multiple times), so that it becomes possible to reliably deliver the drug to the target.

(4) By forming a nanostructure with a material excellent in terms of biocompatibility (for example, blood compatibility), the biocompatibility of the surface of the medical instrument can be improved.

BRIEF DESCRIPTION OF DRAWINGS

FIG. 1 is a schematic cross-sectional view showing a balloon that is the medical instrument according to one embodiment.

FIG. 2(A) and FIG. 2(B) are schematic views showing the behavior of dissociation (release) of a nanostructure by light irradiation. FIG. 2(B) shows a medical instrument, in which a photosensitive portion of a photosensitive linker is photocleaved by light irradiation, and as a result, the nanostructure is dissociated (released).

FIG. 3(A) shows a schematic view of a core-shell-type polymeric micelle, in which Cy5 used as a model reagent is enclosed, and a schematic view of polymers that constitute the polymeric micelle.

FIG. 3(B) shows a reaction between a latex bead (PC-Latex-1), into the surface of which a photocleavable linker having a DBCO group on the surface layer thereof is introduced, and a polymeric micelle.

FIG. 3(C) shows a latex bead (Micelle-PC-Latex-1), on the surface of which a polymeric micelle is immobilized via a photocleavable linker.

FIG. 3(D) shows a latex bead (Micelle-PC-Latex-1), on the surface of which a polymeric micelle is immobilized via a photocleavable linker. FIG. 3(C) is an enlarged view of FIG. 3(D).

FIG. 4 is a view showing the results obtained by measuring the particle size distribution of the polymeric micelle produced in Example 1 according to a dynamic light scattering (DLS) method.

FIG. 5 shows fluorescence images of the Micelle-PC-Latex-1 obtained in Example 1, which are obtained by a confocal laser scanning microscope. FIG. 5(A) shows a fluorescence image obtained before laser light irradiation at 365 nm, and FIG. 5(B) shows a fluorescence image obtained after laser light irradiation at 365 nm.

FIG. 6 shows fluorescence images obtained by a confocal laser scanning microscope, which are for use in evaluating the behavior of Cy5 released by light irradiation that is to be incorporated into a cell. FIG. 6(A) shows the fluorescence image of a cell nucleus stained with the fluorescent dye (Hoechest33342) before light irradiation, which is obtained by a confocal laser scanning microscope; FIG. 6(B) shows the fluorescence image of Cy5 incorporated into a cell before light irradiation, which is obtained by a confocal laser scanning microscope; and FIG. 6(C) shows the bright field image of a cell before light irradiation, which is obtained by a confocal laser scanning microscope. FIG. 6(D) shows the fluorescence image of a cell nucleus stained with the fluorescent dye (Hoechest33342) after light irradiation, which is obtained by a confocal laser scanning microscope; FIG. 6(E) shows the fluorescence image of Cy5 incorporated into a cell after light irradiation, which is obtained by a confocal laser scanning microscope; and FIG. 6(F) shows the bright field image of a cell after light irradiation, which is obtained by a confocal laser scanning microscope.

DESCRIPTION OF EMBODIMENTS

Hereinafter, the present invention will be described in detail in the following embodiments, examples, etc. However, the present invention is not limited to the following embodiments, examples, etc., and the present invention may be arbitrarily modified and carried out within a range that is not deviated from the spirit of the present invention. All documents and publications cited in the present description are incorporated herein by reference in their entirety, regardless of the purposes thereof. It is to be noted that the dimensional ratios used in the drawings are exaggerated for the convenience of explanation, and thus, the dimensional ratios used in the drawings may be different from the actual ratios in some cases.

The term "nanostructure" indicates a structure having a nanometer-scale size (for example, 1 to 1000 nm). The structure means an aggregate of substances each having a two-dimensional or three-dimensional structure. The structure may be either a hollow (for example, the inner side of a core is a hollow), or a solid. The structure may also be multilayered with a hollow layer(s) and a solid layer(s).

The nanostructure can be utilized as a carrier (drug carrier) for drug delivery. In the present description, the phrase "for drug delivery" means that the carrier is biocompatible, and that a drug can be loaded on the carrier.

The material of the nanostructure is not particularly limited, and examples of the material may include various substances such as a polymer, a lipid, a metallic material, an oxide, a ceramic, a magnetic material, a carbon, a silica, a surfactant, and a nanodiamond. The shape of the structure is not particularly limited, and the shape may be a sphere, a non-sphere, an ellipse, a rod, a pyramid, a cube, a disk, a wire, an uneven shape, or a lamellar shape. In general, examples of the polymer may include polymers known in the present technical field, which are for use in producing nanostructures, such as a block copolymer, poly(lactic acid), poly(lactic acid-co-glycolic acid), polyethylene glycol (PEG), an acrylic acid polymer, and a cationic polymer. Examples of the lipid may include fat, wax, sterol, cholesterol, fat-soluble vitamin, monoglyceride, diglyceride, phospholipid, sphingolipid, glycolipid, cationic lipid or anionic lipid, derivatized lipid, and cardiolipin.

The term "to load" means a state in which a drug is contained in a nanostructure, and/or a state in which a drug adheres or binds to a nanostructure by a chemical and/or physical means. A representative example of the above-described chemical means is a chemical bond. Specific examples of such a chemical bond may include a covalent bond, a metallic bond, a coordinate bond, an ionic bond, a hydrogen bond, and an intermolecular force. As the above-described physical means, any given appropriate fixing means other than the chemical means may be adopted. Specific examples of such a physical means may include adsorption, embedding, and impregnation.

The term "micelle" means a vesicle formed with a single layer of molecular membrane. The micelle may be, for example, a micelle formed with an amphipathic molecule such as a surfactant.

The term "polymeric micelle" means an aggregate of polymers, which is formed by self-association of block copolymers constituted with polymer chains having different physiochemical properties such as hydrophilicity, hydrophobicity and electric charge (diblock or multiblock copolymers each having one or more blocks having different physiochemical properties). Typically, the polymeric micelle is a nanoparticle having a core-shell structure formed by autonomous multimolecular association of block copolymers, in each of which a hydrophilic polymer chain is linked to a hydrophobic chain. Typically, the polymeric micelle is a particle having a particle diameter of approximately 10 to 100 nm, in which a hydrophobic portion forms a core and a hydrophilic portion forms a shell in an aqueous medium.

Moreover, the polymeric micelle also includes a polyion complex micelle formed by using electrostatic interaction as a driving force, and a micelle formed by using a metal complex as a driving force. The "polyion complex" (hereinafter referred to as "PIC") is a particulate polymer aggregate formed by autonomous multimolecular association of a block copolymer in which a hydrophilic polymer chain is linked to an anionic polymer chain, with a block copolymer in which a hydrophilic polymer chain is linked to a cationic polymer chain (e.g. polyglutamic acid, polyaspartic acid, etc.), according to electrostatic interaction used as a driving force. Specifically, the polyion complex is a particulate aggregate having a particle diameter of approximately several tens of nm, in which an ionic layer formed between the anionic polymer chain and cationic polymer chain of the two block copolymers forms a core and a hydrophilic portion forms a shell in an aqueous medium. Such a polyion complex is disclosed, for example, in JP Patent Publication (Kokai) No. 8-188541 A (1996) and International Publication No. WO2006/118260.

The term "liposome" means a vesicle formed with two layers of molecular membranes. The molecular membrane is generally a double membrane of phospholipid.

The "polymersome" means a closed endoplasmic reticulum, namely, a vesicle, having a bilayered molecular membrane structure formed from an amphipathic block copolymer (a diblock or multiblock copolymer having one or more hydrophobic blocks and one or more hydrophilic blocks).

The term "nanogel" means a nanoparticle having a hydrogel structure with a nanometer-scale size (for example, 1 to 1000 nm). The nanogel has a three-dimensional network structure of polymer chains that are crosslinked via an electrostatic interaction, a van der Waals force, a hydrophobic interaction, a hydrogen bond, a covalent bond, etc.

The term "nanoparticle" means a fine particle having a nanometer-scale diameter (for example, 1 to 1000 nm, or 1 to 500 nm, or 1 to 100 nm, or 1 to 50 nm, or 1 to 30 nm, 20 nm to 500 nm, or 30 nm to 500 nm, or 20 nm to 200 nm, or 30 to 200 nm, or 20 nm to 100 nm, or 30 nm to 100 nm).

The term "nanorod" means a rod-shaped fine particle, in which the length of a short axis is different from the length of a long axis. Typically, the nanorod is a particle having a short axis (diameter) of approximately 10 to 100 nm and a long axis (length) of approximately 10 to 1000 nm.

The term "nanosphere" means a nanoparticle, in which polymers are aggregated. Typically, the nanosphere is a nanoparticle, in which a drug or the like is enclosed in a matrix comprising a biocompatible polymer as a base material.

1. Medical Instrument

One embodiment of the present invention relates to a medical instrument that is inserted into an affected area or tissue to perform treatment, wherein a drug-loaded nanostructure is covalently bound to the medical instrument via a photosensitive linker immobilized on the surface of at least a portion of the medical instrument.

The medical instrument is not particularly limited, as long as it is inserted into an affected area or tissue (which is simply referred to as a "target site" at times) to perform treatment. Examples of the medical instrument may include a balloon, a catheter, a stent, and a probe.

The affected area or tissue, into which the medical instrument is to be inserted, is not particularly limited, either. Examples of the affected area or tissue may include intravascular sites or intraluminal sites in bodies (e.g. lymphatic vessels; conduits such as bile ducts; digestive tracts; and pathways such as urinary tracts). Specifically, the affected area or tissue is at least one selected from among coronary vascular system, peripheral vascular system, cerebrovascular system, esophagus, airway, sinus, trachea, colon, bile duct, urinary tract, prostate, intracerebral duct, and lower limbs (e.g. femur, blood vessels in the legs, etc.).

In one embodiment, the affected area or tissue is a tissue having a risk of restenosis. In one embodiment, the medical instrument is configured to deliver at least one type of drug to a site having a risk of restenosis. In one embodiment, the medical instrument is configured to deliver at least one type of drug to an intraluminal site including blood clotting or embolism. In one embodiment, the medical instrument is at least one angioplasty balloon, catheter, stent, or probe, which is configured for temporal or permanent indwelling.

The drug is not particularly limited. Examples of the drug used herein may include drugs (e.g. a low molecular weight compound, a peptide, an antibody, a nucleic acid, etc.), pharmaceutical products (e.g. a low molecular weight pharmaceutical product, an antibody pharmaceutical product, a nucleic acid pharmaceutical product, a protein preparation, a vaccine, etc.), diagnostic drugs, and nutritional supplements. The drug can be used alone as a single type, or as a mixture of two or more types.

The drug may be either a water-soluble or water-insoluble drug. In one embodiment, the drug is soluble in water. Conventionally, since such a water-soluble drug has been easily flown into the blood or enzymatically decomposed, it has been difficult to deliver the water-soluble drug to the target site. In the present embodiment, however, it is possible to stably deliver such a water-soluble drug to the target site by loading (e.g. enclosing or encapsulating) the drug on a nanostructure.

The nanostructure is not particularly limited, as long as it is able to load a drug thereon. Examples of the nanostructure may include a micelle, a polymeric micelle, a liposome, a nanorod, a nanogel, a nanoparticle, and a nanosphere.

The form of loading a drug on the nanostructure is not particularly limited. In one embodiment, the drug is contained in the nanostructure. In one embodiment, the drug adheres or binds to the nanostructure by a chemical and/or physical means. In one embodiment, the drug is enclosed in the nanostructure, or physically or chemically binds to the nanostructure.

The size of such a nanostructure is not particularly limited. From the viewpoint of incorporation of the nanostructure into a target cell, the size of the nanostructure is, for example, 500 nm or less, or 200 nm or less, or 100 nm or less, or 50 nm or less. On the other hand, from the viewpoint of loading a necessary amount of drug thereon, the size of the nanostructure is 20 nm or more, or 30 nm or more, or 50 nm or more, or 100 nm or more. In one embodiment, the size of the nanostructure is preferably 20 nm to 500 nm, more preferably 30 nm to 500 nm, even more preferably 30 to 200 nm, and further preferably 30 to 100 nm.

In the present description, the size of a nanostructure indicates a hydrodynamic diameter (mean particle diameter). The hydrodynamic diameter (mean particle diameter) can be measured according to dynamic light scattering (DLS) measurement, and in general, a volume mean diameter is used.

The medical instrument according to one embodiment of the present invention is a balloon. FIG. 1 is a schematic view showing a balloon that is the medical instrument according to one embodiment. Moreover, FIG. 2(A) and FIG. 2(B) are schematic views showing the behavior of dissociation (release) of a nanostructure from the medical instrument by light irradiation. Hereafter, the balloon shown in these figures will be taken as an example and will be described, but the medical instrument of the present invention is not limited to this embodiment.

A medical instrument 1 has photosensitive linkers 12 immobilized on parts of the outer surface thereof. Nanostructures 11 bind to the outer surface 13 of the medical instrument (balloon) mediated by the photosensitive linkers 12 via covalent bonds. In one embodiment, a covalent bond is formed between a functional group existing on the outer surface 13 of the medical instrument (balloon) and a functional group existing in the photosensitive linker 12, and further, a covalent bond is formed between a functional group existing in the photosensitive linker 12 and a functional group existing in the nanostructure 11. As such, since the nanostructure 11 is immobilized on the outer surface 13 of the medical instrument (balloon), dissociation and outflowing of the nanostructure and/or the drug due to blood flow or the like are suppressed or prevented in a process in which the medical instrument arrives at the target site, so that the drug can be stably delivered to the target site.

The surface 13 of the medical instrument (balloon) may be coated to improve biocompatibility. Otherwise, the surface layer portion of the nanostructure 12 can be constituted with a material excellent in terms of biocompatibility (for example, polyethylene glycol (PEG), etc.). By adopting such an embodiment, the improvement of biocompatibility due to the use of nanostructures can be expected, and the step of coating the surface of the medical instrument can be omitted or simplified.

The photosensitive linker 12 has a photosensitive portion **12*a* that is cleaved or decomposed by being exposed to a light. As shown in FIG. 2(A), by exposing the photosensitive linker 12 to light (hv), the photosensitive portion 12*a* is cleaved or decomposed as shown in FIG. 2(B). As shown in FIG. 2(B), the photosensitive linker 12** is disconnected by the cleavage or decomposition of the photosensitive portion 12*a*, and the nanostructure 11 and/or a drug loaded on the nanostructure 11 (not shown in the figures) is thereby released to a site nearest to the disconnected site.

In one embodiment, the nanostructure is a polymeric micelle. FIG. 3(A) is a schematic view of the polymeric micelle according to one embodiment. In FIG. 3(A), the left view shows a polymeric micelle 21, and the right view shows individual constituents of the polymeric micelle 21. As shown in FIG. 3(A), the polymeric micelle 21 is configured to comprise block copolymers 22. The block copolymer is configured to comprise a hydrophilic polymer chain (PEG) and a polymer chain (PAsp or PDAP). The block copolymers are aligned radially, such that the hydrophilic polymer chains are disposed outside, thereby forming a micelle. A drug 24 is enclosed in the core portion of the micelle. That is to say, the polymeric micelle 21 has a core-shell structure, in which the polymer chain in the block copolymer 22 and the drug 24 form a core portion and the hydrophilic polymer chain in the polymer 22 is extended to outside to form a shell portion. This polymeric micelle 21 is excellent in terms of biocompatibility (stability in the blood), since it has a hydrophilic polymer chain in the shell portion thereof.

The micelle shown in FIG. 3(A) is configured, such that the hydrophilic polymer chain as a part of the block copolymer 22 is modified with functional groups 25, and that the functional groups 25 are present on the surface layer of the micelle 21. In addition, as shown in FIG. 3(B) and FIG. 3(C), in the polymeric micelle 21, a covalent bond is formed between the functional group 25 of the surface layer and the functional group of a photosensitive linker 32 immobilized on the surface of a medical instrument 33, and thereby, the polymeric micelle 21 can be immobilized on the surface of the medical instrument. The photosensitive linker 32 has a photosensitive portion 32*a*, and by exposing the photosensitive linker 32 to light (hv), the photosensitive portion 32*a* can be cleaved or decomposed.

The block copolymer that constitutes the polymeric micelle is not particularly limited, and a block copolymer that is generally well-known in the present technical field can be used.

An example of the block copolymer is a block copolymer constituted with a hydrophilic polymer chain and polyamino acid.

The hydrophilic polymer chain can be constituted with any given appropriate hydrophilic polymer. Examples of the hydrophilic polymer may include poly(ethylene glycol), polysaccharide, poly(vinyl pyrrolidone), poly(vinyl alcohol), poly(acrylamide), poly(acrylic acid), poly(methacrylamide), poly(methacrylic acid), poly(methacrylic acid ester), poly(acrylic acid ester), hydroxyethyl polyacrylate, poly(hydroxyethyl methacrylate), polyamino acid, poly (malic acid), poly(2-methyl-2-oxazoline), poly(2-ethyl-2-oxazoline), poly(2-isopropyl-2-oxazoline), and derivatives thereof. Specific examples of the polysaccharide may include starch, dextran, fructan, and galactan. Among these, poly(ethylene glycol) (PEG) can be preferably used because terminus-reactive polyethylene glycols having various functional groups at the termini thereof are commercially available, and also, polyethylene glycols having various molecular weights are commercially available, and thus, poly (ethylene glycol) (PEG) can be easily obtained. The terminus of PEG (polyethylene glycol) may be methoxylated (MPEG; methoxy(polyethylene glycol)). These hydrophilic polymer chains can be used alone as a single type, or as a mixture of two or more types.

Examples of the polyamino acid may include: non-polar amino acids such as leucine, isoleucine, phenylalanine, methionine, and tryptophan; acidic amino acids such as aspartic acid and glutamic acid; basic amino acids such as lysine, ornithine, arginine, homoarginine, and histidine; derivatives thereof; and a polymer of amino acids selected from these combinations.

The polymeric micelle can be formed using the above-described block copolymers and conventionally known block copolymers according to a publicly known method. Besides, in the embodiment shown in FIG. 3(A), the drug 24 is immobilized on the polymeric micelle by being modified (bound) to a part of the block copolymer 22. However, the drug 24 does not need to be bound to the block copolymer 22.

For example, in the case of a drug-loaded polymeric micelle, for example, a solution in which drugs are dissolved in a solvent such as alcohol, and a solution in which block copolymers are dissolved in a pH buffer, are prepared separately, and thereafter, the two solutions are mixed with each other, and the mixed solution is then dialyzed against PBS, so as to produce a polymeric micelle comprising the drugs and the block copolymers (e.g. a polymeric micelle, in which the drugs are enclosed in the core portion thereof). Even in the case of a PIC micelle or a liposome, a solution comprising polymers forming the PIC micelle or the liposome and a solution comprising drugs are prepared, and the two solutions are then mixed by stirring, so that the drugs are enclosed in the PIC micelle or the liposome. Alternatively, a solution comprising block copolymers is stirred to form a polymeric micelle or a PIC micelle, and a solution in which drugs are dissolved is then added to the micelle solution, so that the drugs can be enclosed in the micelle.

The nanostructure is not limited to the above-exemplified polymeric micelle constituted with block copolymers, and a polymeric micelle constituted with lipid molecules, a liposome, a polymersome, a nanogel, a nanoparticle, a nanorod, a nanosphere, etc. can also be used.

The photosensitive linker is not particularly limited, as long as it comprises a photosensitive portion and is able to immobilize the nanostructure on the surface of the medical instrument. Such immobilization can be mediated by, for example, one or multiple covalent bonds.

In one embodiment, the photosensitive linker has a photosensitive portion, a functional group capable of forming a covalent bond with a functional group existing in the nanostructure (hereinafter also referred to as a "first functional group"), and a functional group capable of forming a covalent bond with a functional group existing on the surface of the medical instrument (hereinafter also referred to as a "second functional group"). The nanostructure is immobilized on the surface of the medical instrument mediated by the photosensitive linker, via the bond between the first functional group and the functional group existing in the nanostructure, and the bond between the second functional group and functional group existing on the surface of the medical instrument.

From the viewpoint of the reactivity between the nanostructure and the photosensitive linker, the functional group is preferably introduced into the surface layer of the nanostructure. After production of the nanostructure, the surface thereof may be modified, and the functional group may be then introduced therein. Otherwise, a nanostructure in which a functional group exists on the surface layer thereof can be formed by using molecules modified with functional groups. For example, as in the case of the polymeric micelle shown in FIG. 3(A), by using block copolymers, in which the terminus of the hydrophilic polymer chain is modified with the functional group, as some block copolymers constituting a polymeric micelle, it is possible to form a polymeric micelle having the functional group on the surface layer portion thereof.

The combination of the above-described first functional group and the functional group of the nanostructure is not particularly limited, as long as the nanostructure can be stably immobilized via a covalent bond between the two functional groups. Examples of the combination of the first functional group and the functional group of the nanostructure may include a DBCO group and an azide group ($—N_3$), a carboxyl group and an amino group, and a thiol group and a maleimide group.

The method of modifying the surface of the medical instrument with a functional group is not particularly limited, and it may be determined depending on the material of the surface of the medical instrument. For example, for the surface of the medical instrument made of a polymer or a rubber material, a functional group created on the surface of a polymer according to a corona or plasma technique, such as, for example, an amino group or an aldehyde group, can be used.

The combination of the second functional group and the functional group on the surface of the medical instrument is not particularly limited, and those generally used in the present technical field can be utilized. Examples of the combination of the second functional group and the functional group on the surface of the medical instrument may include a DBCO group and an azide group, a carboxyl group and an amino group, and a thiol group and a maleimide group.

The photosensitive portion is a site that is cleaved or decomposed by being exposed to light. In a specific embodiment, the photosensitive linker (photosensitive portion) is cleaved or decomposed by being exposed to a light with a wavelength of 200 to 1000 nm. In one embodiment, the photosensitive linker (photosensitive portion) is cleaved or decomposed by being exposed to a light (ultraviolet ray) with a wavelength of 200 to 380 nm. In one embodiment, the photosensitive linker (photosensitive portion) is cleaved or decomposed by being exposed to a light (visible light) with a wavelength of 380 to 700 nm. In one embodiment, the photosensitive linker (photosensitive portion) is cleaved or decomposed by being exposed to a light (infrared ray) with a wavelength of 700 to 1000 nm.

The number of the photosensitive linkers to be introduced into the surface of the medical instrument is not particularly limited, and it may be 1 or 2 or more.

The medical instrument may comprise two or more types of photosensitive linkers (photosensitive portions) that are cleaved or decomposed with lights having different wavelengths. By allowing the medical instrument to comprise such two or more types of photosensitive linkers (photosensitive portions), it becomes possible to perform the stepwise release of nanostructures and drugs, the release of nanostructures and drugs in different target sites, and the simultaneous or stepwise release of multiple drugs in different target sites.

The photosensitive linker is not particularly limited, as long as it comprises a photosensitive portion. For example, the photosensitive portion has a structure represented by the following formula (I):

(I)

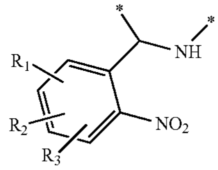

In the above formula (I), * represents a binding site.

In the above formula (I), $R_1$, $R_2$, and $R_3$ each independently represent a hydrogen atom, lower alkyl (e.g. linear or branched alkyl containing 1 to 6 carbon atoms (preferably 1 to 4 carbon atoms)), lower alkoxy (e.g. linear or branched alkoxy containing 1 to 6 carbon atoms (preferably 1 to 4 carbon atoms)), amino, a halogen atom (F, Cl, Br, or I), hydroxy or cyano, or any two of the adjacent $R_1$, $R_2$, and $R_3$ together form a methylenedioxy group.

In one embodiment, all of $R_1$, $R_2$, and $R_3$ are hydrogen atoms. In one embodiment, any two of $R_1$, $R_2$, and $R_3$ are hydrogen atoms, and the remaining one is a hydrogen atom, lower alkyl, or lower alkoxy.

In the structure represented by the above formula (I), the C—N bond in the formula (I) can be dissociated, for example, by light irradiation with a wavelength of 365 nm (deprotection of an o-nitrobenzyl group). Accordingly, when the photosensitive portion comprises the structure of the above formula (I), a light with a specific wavelength range, having a peak around 365 nm, for example, a laser light or an ultraviolet ray having a wavelength range of 360 to 370 nm, 355 to 375 nm, 350 to 380 nm, 345 to 385 nm, 340 to 390 nm, etc. can be utilized in the cleavage of the photosensitive linker.

In one embodiment, the photosensitive linker comprises a structure derived from a photosensitive unit comprising 3-amino-3-(2-nitrophenyl)propanoic acid (ANP).

Another example of the photosensitive linker is a photosensitive linker comprising at least one selected from among a double bond that binds two carbon atoms to each other, an azo bond, a peroxide bond, and a bond that binds a carbon atom to a nitrogen atom.

For instance, a photosensitive (photodissociable) protecting group containing the above-described bond can be utilized as a photosensitive portion. By deprotecting the protecting group by light irradiation, the photosensitive linker is cleaved. Examples of such a photodissociable protecting group may include one or more selected from among α-substituted acetophenone, 3'-5'-dimethoxybenzoin, benzyl group, cinnamic acid ester, coumaryl-methyl-diethyl phosphate, o-nitrobenzyl ester, and analogs thereof.

For instance, deprotection of polycyclic aromatic hydrocarbons (aqmoc, mcmoc, and phmoc) can be carried out by using a light source with a wavelength of 350 nm, or a light source providing a wavelength of, for example, 345 to 355 nm, 340 to 360 nm, 335 to 365 nm, 330 to 370 nm, etc.

It is possible to utilize deprotection involving cis-trans isomerization relating to coumarin (366 nm), vinylphenol (254 nm), and vinylnaphthol (350 nm) (wherein the wavelength in the parentheses is a wavelength proving the maximum deprotection).

Deprotection of a silyl group can be carried out using lights with wavelengths of 204 nm and 254 nm.

Deprotection of N-methyl-N-(o-nitro)carbamate can be carried out using a light with a wavelength of 254 nm.

Deprotection of a 2-benzylbenzoic acid group can be carried out using a light with a wavelength of 300 to 390 nm.

Deprotection of a 3,5-dimethoxybenzoin (3,5-DMB) derivative can also be utilized. A molecule having a functional group that is a carboxylic acid is protected by a reaction with 3,5-DMB, and is able to give an ester. A molecule having a functional group that is a secondary amine is protected by a reaction with 3,5-DMB, and is able to give a carbamate.

A commercially available product may be used as such a photosensitive linker, and 3-AMINO-3-(2-NITROPHENYL)PROPIONIC ACID (product name) manufactured by MARK, etc. can be used.

The wavelength and intensity of a light to be applied to the photosensitive linker is not particularly limited, as long as the photosensitive portion is cleaved or decomposed by being exposed to the light. Thus, the wavelength and intensity of a light to be applied to the photosensitive linker are determined, as appropriate, depending on the structure and/or type of the photosensitive portion. Examples of the intensity of an irradiation light may include 0.01 to 0.02 $mW/cm^2$, 0.02 to 0.05 $mW/cm^2$, 0.05 to 0.1 $mW/cm^2$, 0.1 to 0.2 $\mu W/cm^2$, 0.2 to 0.5 $\mu W/cm^2$, 0.5 to 1.0 $\mu W/cm^2$, 1.0 to 2.0 $\mu W/cm^2$, 2.0 to 5.0 $\mu W/cm^2$, 5.0 to 10 $\mu W/cm^2$, 10 to 20 $\mu W/cm^2$, 20 to 50 $\mu W/cm^2$, 50 to 100 $\mu W/cm^2$, 100 to 200 $\mu W/cm^2$, 200 to 500 $\mu W/cm^2$, 500 to 1000 $\mu W/cm^2$, 1 to 2 $mW/cm^2$, 2 to 5 $mW/cm^2$, 5 to 10 $mW/cm^2$, 10 to 20 $mW/cm^2$, 20 to 50 $mW/cm^2$, 50 to 100 $mW/cm^2$, 100 to 200 $mW/cm^2$, 200 to 500 $mW/cm^2$, 500 to 1000 $mW/cm^2$, and any given combinations thereof. The light may be either a continuous light or a pulsed light. The irradiation time is not particularly limited, as long as it is sufficient for the cleavage or decomposition of the photosensitive portion by light exposure. Examples of the irradiation time may include about 0.01 millisecond, about 0.02 milliseconds, about 0.05 milliseconds, about 0.1 millisecond, about 0.2 milliseconds, about 0.5 milliseconds, about 1.0 millisecond, about 2 milliseconds, about 5 milliseconds, about 10 milliseconds, about 20 milliseconds, about 50 milliseconds, about 100 milliseconds, about 200 milliseconds, about 500 milliseconds, about 1 second, about 2 seconds, about 5 seconds, about 10 seconds, about 20 seconds, about 50 seconds, about 100 seconds, about 1 minute, about 2 minutes, about 10 minutes, about 20 minutes, about 40 minutes, about 60 minutes, about 2 hours, and about 4 hours.

The medical instrument according to the embodiment of the present invention further comprises a light source for exposing the photosensitive linker to a light. In one embodiment, the light source is selected from a light-emitting diode and a semiconductor laser. From such a light source, a light effective for the photocleavage of the photosensitive linker (side light emission) can be delivered to a target site.

The light source can be used in any given place, in which a light is delivered to the photosensitive linker on the surface of the medical instrument. For example, the light source is used in a target site close to the photosensitive linker, or in a tissue in the body that is different from the site in which the photosensitive linker is present, or outside the body, so that a light effective for the photocleavage of the photosensitive linker (side light emission) can be delivered. The light source is configured to generate a light with any given appropriate wavelength. Substantial examples of such a light with an appropriate wavelength may include ultraviolet ray, visible lights, namely, violet, blue, green, yellow, orange and red, and infrared ray, or any given combinations of these two or more types, which are provided, for example, by different optical cables, or at different time points.

The medical instrument according to one embodiment of the present invention further comprises a secondary medical instrument for exposing the above-described photosensitive linker to a light. The secondary medical instrument may be, for example, a secondary instrument having at least one optical fiber or photonic crystal fiber that delivers to the photosensitive linker, a light effective for photocleavage generated by the light source. Furthermore, one embodiment of the present invention relates to the above-described medical instrument that is present as a unit integrated with the secondary medical instrument. One embodiment of the present invention relates to a kit comprising the above-described medical instrument, and the secondary medical instrument having at least one optical fiber or photonic crystal fiber that delivers to the photosensitive linker, a light effective for the photocleavage of the photosensitive linker. In a specific embodiment, the above-described medical instrument is a balloon, and there is provided a kit comprising this medical instrument and the secondary medical instrument having at least one optical fiber that delivers to the photosensitive linker, a light effective for the photocleavage of the photosensitive linker. In a specific embodiment, the above-described medical instrument is a balloon, which is configured such that a nanostructure is present while the nanostructure is allowed to come into contact with the blood wall as a result of balloon dilatation.

2. Method for Producing Medical Instrument

The medical instrument according to the above-described embodiment can be produced by (1) immobilization of a photosensitive linker on the surface of the medical instrument, and (2) immobilization of a nanostructure on the photosensitive linker. The order of performing the above-described process (1) and process (2) is not particularly limited, and the processes (1) and (2) may be carried out simultaneously.

For example, when process (2) is carried out after completion of process (1), the medical instrument can be produced by the following steps.

First, the second functional group of the photosensitive linker is allowed to react with and bind to a functional group present on the surface of the medical instrument, so that the photosensitive linker is immobilized on the surface of the medical instrument. This reaction is carried out, for example, by applying a solution containing the photosensitive linker onto the surface of the medical instrument, or by immersing the medical instrument in the aforementioned solution.

Thereafter, the first functional group of the photosensitive linker immobilized on the surface of the medical instrument is allowed to react with a functional group existing in a nanostructure, so that the functional groups are covalently bound to each other. This reaction is carried out, for example, by applying a solution containing the nanostructure onto the surface of the medical instrument, or by immersing the medical instrument in the aforementioned solution.

3. Intended use of Medical Instrument

The medical instrument according to the above-described embodiment can be used to deliver a drug-loaded nanostructure and/or a drug to a target site. The medical instrument according to the above-described embodiment can be used as a means for selectively and efficiently introducing a desired drug loaded on the nanostructure to a target site. The medical instrument according to the above-described embodiment is configured, such that a photosensitive linker is cleaved by inserting the medical instrument into a target site and then exposing the medical instrument to a light at the target site, and such that a nanostructure and/or a drug loaded on the nanostructure are thereby released to a site nearest to the target site. In one embodiment, the medical instrument is configured to deliver at least one type of reagent into an intraluminal site or other sites in the body.

According to the medical instrument of the embodiment, a drug is released by the disconnection (cleavage or decomposition) of the photosensitive linker immobilized on the surface thereof due to light exposure. In one embodiment, the release of the drug depends on the intensity or wavelength of a light. In a preferred embodiment, by adjusting the amount or wavelength of a light to be exposed, the release behavior (speed, timing, etc.) of a nanostructure and/or a drug loaded on the nanostructure is controlled.

The present invention includes the delivery of a nanostructure and the delivery of a drug loaded on the nanostructure for the purpose of diagnosis or treatment, in which the medical instrument according to the above-described embodiment is used.

The medical instrument of the present invention is inserted into an affected area or tissue to perform treatment. The present medical instrument can be applied to various types of animals such as a human, a mouse, a rat, a rabbit, a pig, a dog and a cat, and the treatment target is not limited.

One embodiment of the present invention provides a drug delivery device including the medical instrument according to the above-described embodiment. The drug delivery device of the present invention can be used as a mean for selectively and efficiently introducing a loaded desired drug into a target site. In addition, in another embodiment, the present invention provides a method for releasing a loaded desired drug to a target site, using the aforementioned medical instrument.

One embodiment of the present invention relates to a method for delivering or releasing at least one type of drug to an affected area or tissue, using the medical instrument according to the above-described embodiment, wherein the method comprises a step of disposing the above-described medical instrument in an affected area or tissue (for example, an intravascular site or a lumen in the body), and a step of applying to the medical instrument, a light in an amount effective for the disconnection (cleavage or decomposition) of a photosensitive linker.

EXAMPLES

Hereinafter, the present invention will be described in more detail in the following examples, production examples, and test examples. However, the present invention is not limited to these examples.

In the present description, the term "room temperature" generally indicates approximately 10° C. to approximately 35° C. The symbol "%" indicates weight percent, unless otherwise specified.

In the present description, the term "approximately" may mean ±10%.

The abbreviations used in the following examples are common abbreviations well known to those skilled in the art. Several abbreviations are shown below.

FMOC: 9-fluorenylmethyloxycarbonyl

FMOC-ANP: 3-(9H-fluoren-9-ylmethoxycarbonylamino)-3-(2-nitrophenyl)propanoic acid EDC: 1-(3-dimethylaminopropyl)-3-ethylcarbodiimide DBCO: dibenzocyclooctyne PEG: polyethylene glycol PAsp: polyaspartic acid PBS: phosphate-buffered saline The structures of FMOC-ANP and DBCO-PEG4-$NH_2$ used in the examples are as follows.

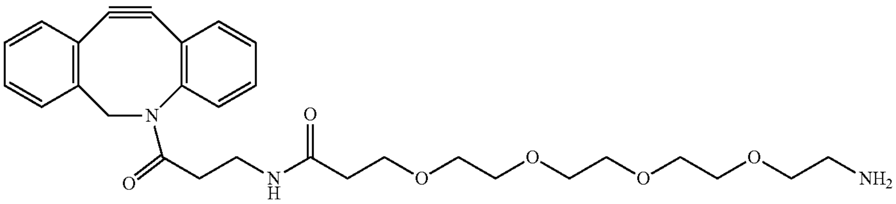

DBC-PEG4-$NH_2$

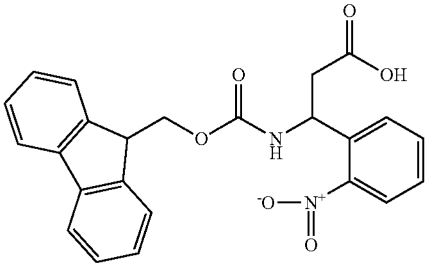

FMOC-ANP

In addition, the structures of $N_3$-PEG-PAsp, MeO-PEG-PAsp-Cy5, and MeO-PEG-PDAP used in the examples are as follows.

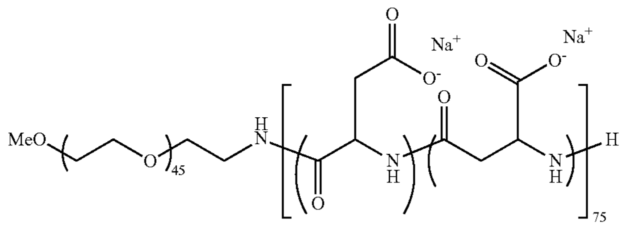

MeO-PEG-PAsp (45-75)

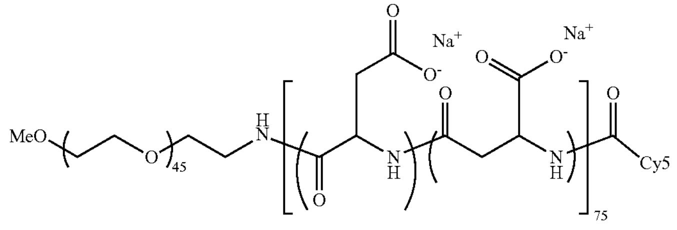

MeO-PEG-PAsp-Cy5 (45-75)

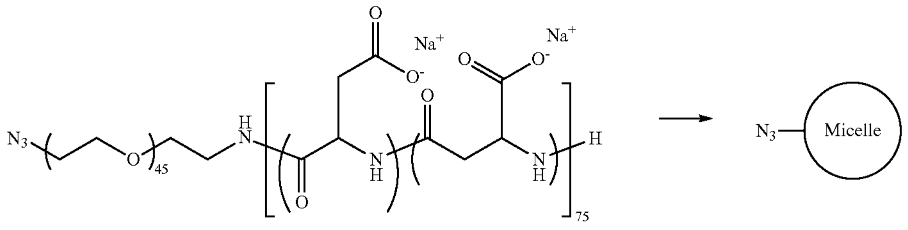

$N_3$-PEG-PAsp (45-75)

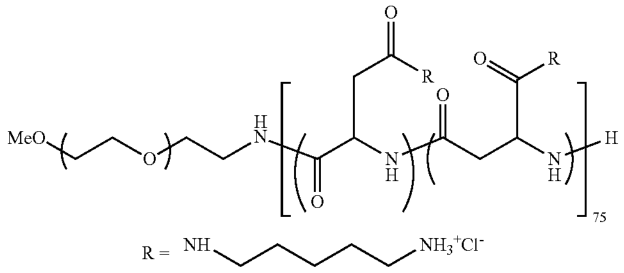

MeO-PEG-PDAP (45-75)

Example 1: Production of Micelle-Loaded Photoresponsive Latex Bead (Micelle-PC-Latex-1)

Hereafter, with reference to FIG. 3(A), FIG. 3(B), Figure (C) and FIG. 3(D), a step of producing the micelle-loaded photoresponsive latex bead (Micelle-PC-Latex-1) produced in Example 1 will be described.

(1) Preparation of Model Micelle Solution $N_3$-PEG-PAsp, MeO-PEG-PAsp-Cy5, and MeO-PEG-PDAP were dissolved at a ratio of 25/25/50 (molar ratio) in a 10 mM phosphate buffer (pH7.4; 0 mM NaCl) to result in a solid concentration of 1 mg/mL, so as to prepare a model micelle solution.

$N_3$-PEG-PAsp is a block copolymer of a PEG chain whose terminus is modified with an azide group ($N_3$—) and a PAsp chain. MeO-PEG-PDAP is a block copolymer of a PEG chain whose terminus is modified with methoxy (MeO—) and a PDAP chain. MeO-PEG-PAsp is a block copolymer of a PEG chain whose terminus is modified with methoxy (MeO—) and a PAsp chain. In a part (50%) of MeO-PEG-PAsp, the N-terminus of the PAsp chain is modified with Cy5, using sulfo-Cy5-NHS (manufactured by Lumiprobe). That is to say, MeO-PEG-PAsp-Cy5 is a block copolymer of a PEG chain, in which the α-terminus of PEG is modified with methoxy (MeO—) and the PAsp terminus is modified with Cy5, and a PAsp chain, wherein the MeO-PEG-PAsp-Cy5 comprises MeO-PEG-PAsp and MeO-PEG-PAsp at a ratio of 50:50 (molar ratio).

As shown in FIG. 3(A), the obtained model micelle solution comprises, in the micelle core thereof, a polymeric micelle (21 in FIG. 3(A)) constituted with a core formed from a PAsp block, in which Cy5 (24 in FIG. 3(A)) as a model reagent is enclosed, and a PDAP block, and a PEG shell having an azide group ($N_3$—) (25 in FIG. 3(A)) on the surface layer thereof.

Employing Zetasizer (manufactured by Malvern), the polymeric micelle was subjected to dynamic light scattering (DLS) measurement using a light at 633 nm. As a result, the size of a micelle (mean particle diameter) was found to be 30 nm. It is to be noted that this size is a volume mean value.

(2) Preparation of Micelle-PC-Latex-1

(i) Step 1: Introduction of Photocleavable Linker (PC) into Surface of Latex Bead (Reaction Scheme 1)

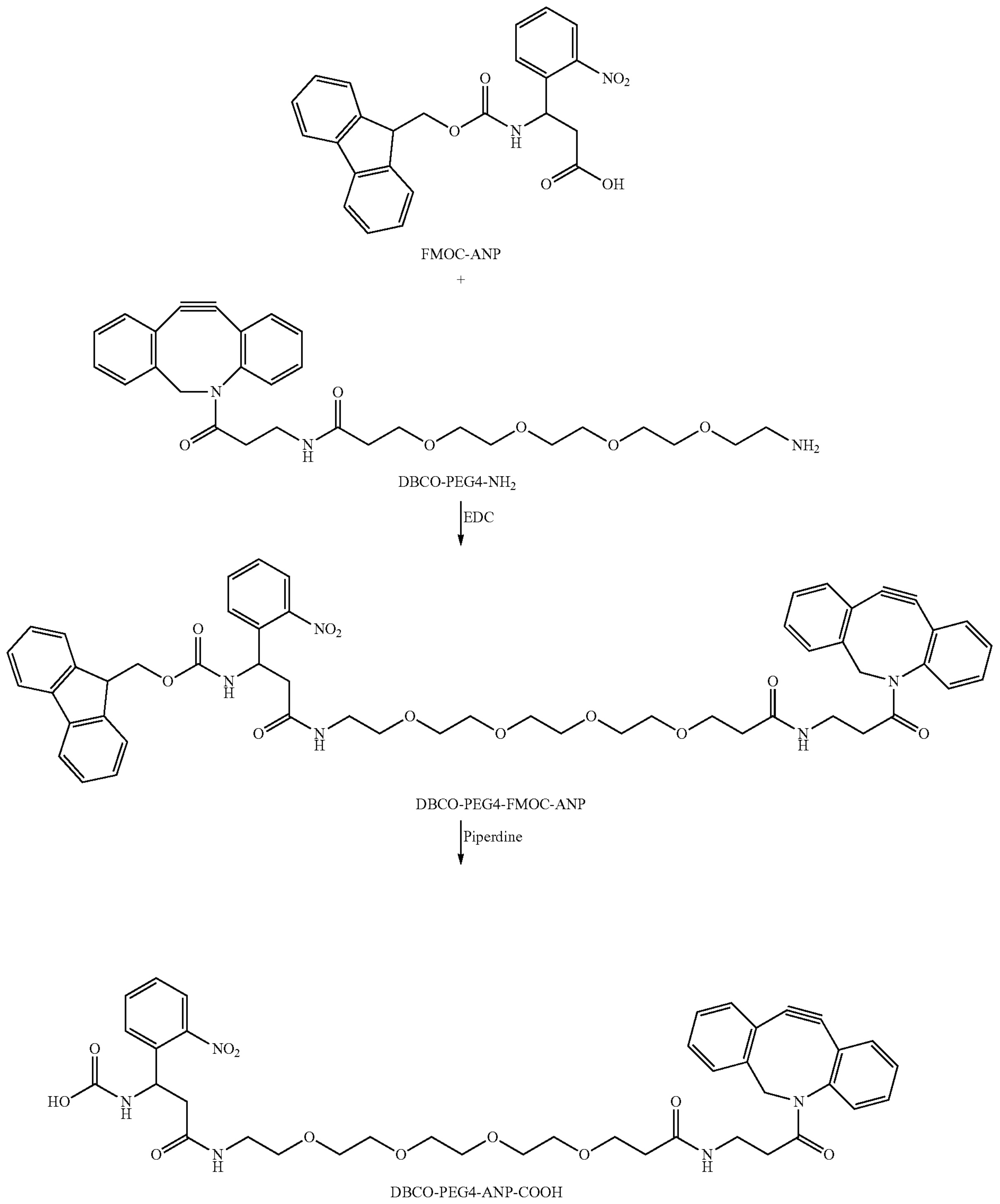

(Reaction Scheme 2)

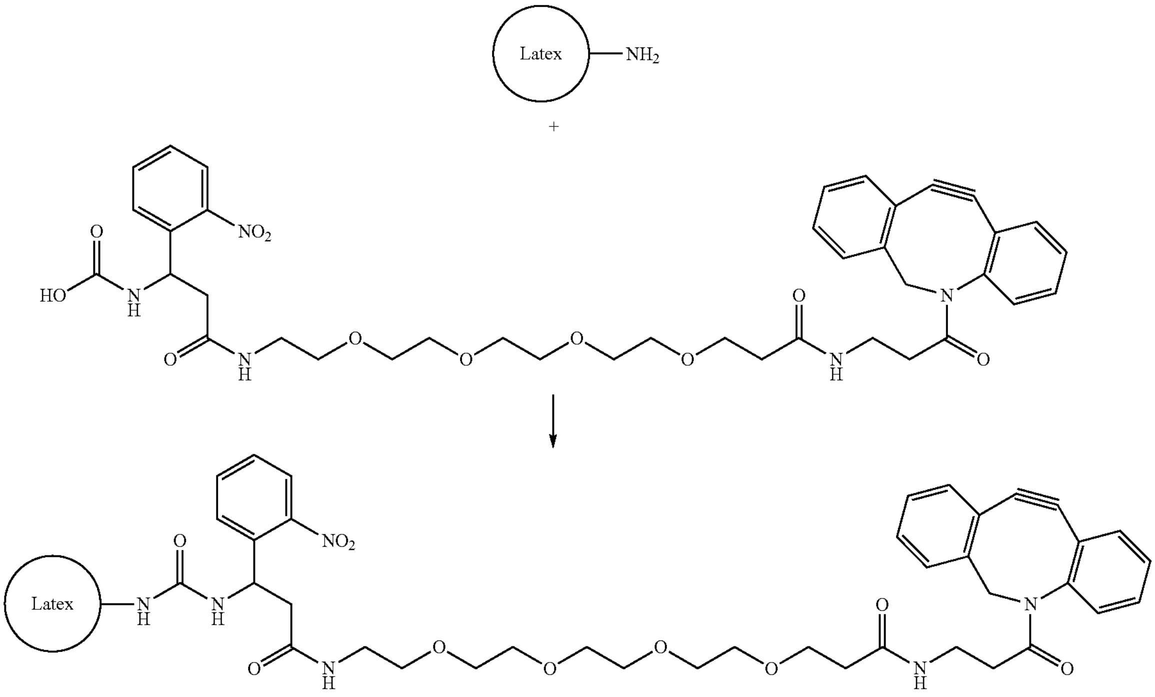

100 μL of Latex-$NH_2$ beads (manufactured by Micromod; product name: Micromer, NH2) were centrifuged, and FMOC-ANP (100 μL, $2.31\times10^{2}$ mM, manufactured by Merck), EDC (5 eq., 44 μL) and urea (3 eq., 100 μL) were then added to the resultant, followed by stirring the obtained mixture for 24 hours. After completion of the reaction, the reaction mixture was purified, and 200 μL of 50% piperidine solution was then added thereto, followed by stirring the obtained mixture for 8 hours. After completion of the purification of the reaction mixture, DBCO-PEG4-$NH_2$ (100 μL, $1.91\times10^{-2}$ mM) and EDC (3 eq., 146 μL) were then added thereto, followed by performing a reaction for 24 hours.

Thereby, PC-Latex-1, in which a photocleavable linker having a DBCO group in the surface layer thereof (DBCO-PEG4-ANP-COOH) (32 in FIG. 3(B)) was introduced onto the surface of the latex bead (33 in FIG. 3(B)), was obtained (FIG. 3(B)).

(ii) Step 2: Loading of Micelle on Latex Bead (Reaction Scheme 3)

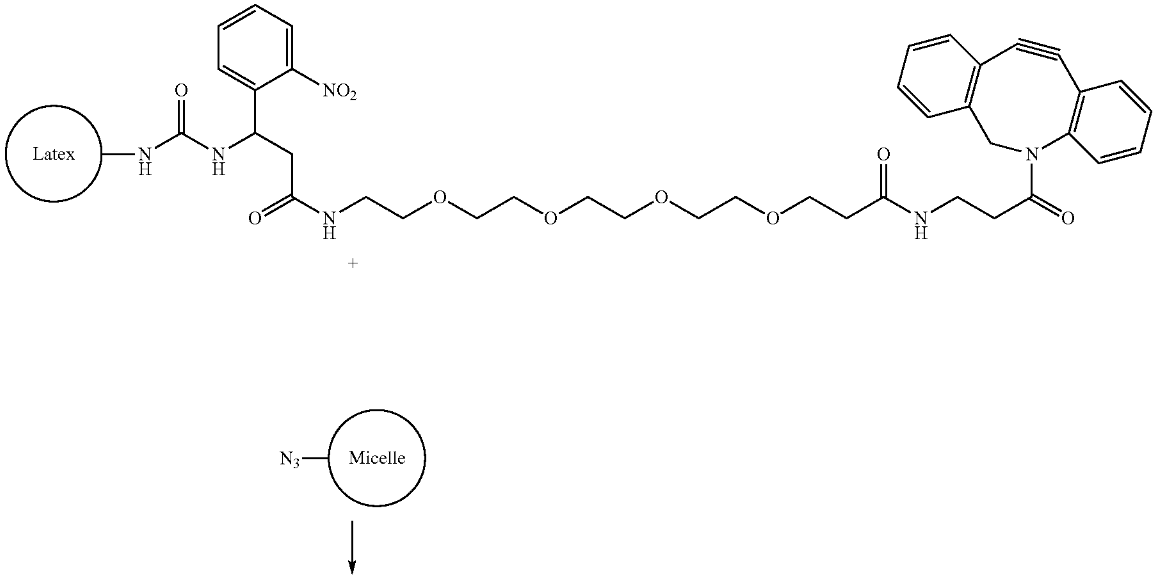

-continued

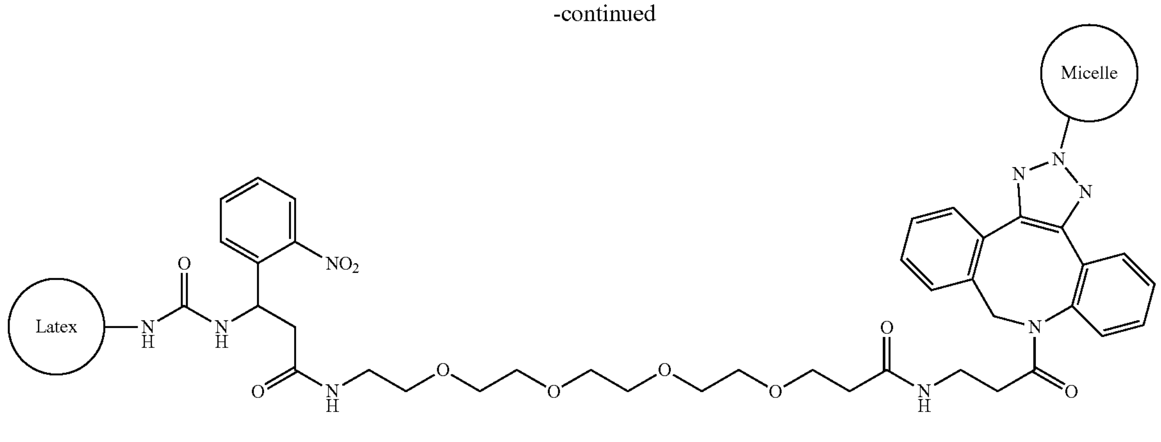

A model micelle solution (100 μL, diluted to 50-fold) was added to the purified beads, and the resultant was freeze-dried and was then thawed at 4° C. After completion of centrifugation and purification, Micelle-PC-Latex-1 was obtained as a product of interest (FIGS. 3(C) and 3(D)). Specifically, as shown in FIGS. 3(B) to (D), the DBCO group in the photocleavable linker 32 immobilized on the surface of the latex was allowed to react with the azide group 25 present in the surface layer of the shell layer of the polymeric micelle 21, so that the polymeric micelle 21 was covalently bound onto the surface of the latex bead 33 via the photocleavable linker 32 and is immobilized thereon.

Example 2: Photocleavage Experiment

The Micelle-PC-Latex-1 obtained in Example 1 was dissolved in 200 μL of $H_2O$ to a concentration of 0.01 mg/μL, so as to prepare a sample solution. A laser with a wavelength of 365 nm was applied to the sample solution at 0.36 W for 40 minutes to perform photocleavage.

Using a confocal laser scanning microscope (LSM800), fluorescence observation was performed on Cy5 (em: 633 nm) as a model reagent enclosed in the micelle, before and after light irradiation with a laser light having a wavelength of 365 nm, so as to confirm introduction of the Cy5-enclosed micelle onto the surface of the latex and photoresponsivity (photocleavage).

Specifically, introduction of the Cy5-enclosed micelle onto the surface of the latex was evaluated by performing fluorescence observation on the micelle before the light irradiation with a laser light having a wavelength of 365 nm, using a confocal scanning microscope. When a micelle can be loaded on the surface of a latex, the fluorescence of Cy5 enclosed in the micelle can be observed by irradiation with a laser at 633 nm. The fluorescence image of the Micelle-PC-Latex-1 obtained in Example 1 (before light irradiation with a laser light having a wavelength of 365 nm) obtained using a confocal laser scanning microscope is shown in FIG. 5(A). As shown in FIG. 5(A), since a circular-shaped fluorescence could be obtained, introduction of the micelle onto the surface of the latex was confirmed.

Furthermore, photoresponsivity was evaluated by performing fluorescence observation on the micelle after the light irradiation with a laser light having a wavelength of 365 nm for 40 minutes, using a confocal scanning microscope (LSM800). This is because ANP that is a photocleavable group (PC) used in the present experiment is cleaved at 365 nm. FIG. 5(B) shows the fluorescence image of the Micelle-PC-Latex-1 obtained in Example 1 after light irradiation with a laser light having a wavelength of 365 nm, obtained using a confocal laser scanning microscope. As shown in FIG. 5(B), it is confirmed that the fluorescence observed before the irradiation (FIG. 5(A)) disappeared. From these results, it is considered that ANP was cleaved by light irradiation with a laser having a wavelength of 365 nm, and that the micelle loaded on the surface of the latex was thereby dissociated, so that the fluorescence of Cy5 enclosed in the micelle could not be observed.

Example 3: Cellular Uptake Experiment

The behavior of Cy5 that is released as a result of the cleavage due to a light irradiation and is to be incorporated into a cell was evaluated using HeLa cells seeded on a 96-well plate. Specifically, the Micelle-PC-Latex-1 obtained in Example 1 was purified with a urea solution and PBS, and was then dissolved in 200 μL of PBS to a concentration of 0.01 mg/μL. A 365 nm laser was applied to the obtained solution at 360 $mW/cm^2$ for 1 minute, and a solution containing a photocleaved micelle was then recovered. The recovered solution was added into the wells, in which the HeLa cells had been cultured, and the obtained mixture was then incubated for 8 hours. The cell nucleus was washed with PBS, and was then stained with the fluorescence reagent Hoechst 33342 (100 μL, 2.2 nM). The behavior of the obtained Cy5 to be incorporated into the cells was evaluated using a confocal laser scanning microscope (LSM800).

Specifically, in order to examine the behavior of the Cy5 to be incorporated into the cells, supernatants recovered before and after the irradiation with a 365 nm laser were each added to the HeLa cells, and the obtained mixtures were then incubated for a predetermined period of time, followed by performing fluorescence observation. FIG. 6(A) shows the fluorescence image of the cell nucleus stained with fluorescent dye (Hoechest33342) before light irradiation, which was obtained using a confocal laser scanning microscope; FIG. 6(B) shows the fluorescence image of Cy5 incorporated into the cell before the light irradiation, which was obtained using a confocal laser scanning microscope; and FIG. 6(C) shows the bright field image of the cell before the light irradiation, which was obtained using a confocal laser scanning microscope. FIG. 6(D) shows the fluorescence image of the cell nucleus stained with fluorescent dye (Hoechest33342) after light irradiation, which was obtained using a confocal laser scanning microscope; FIG. 6(E)

shows the fluorescence image of Cy5 incorporated into the cell after light irradiation, which was obtained using a confocal laser scanning microscope; and FIG. 6(F) shows the bright field image of the cell after light irradiation, which was obtained using a confocal laser scanning microscope.

The fluorescence was not observed in FIG. 6(B), whereas the fluorescence was observed in the cell in the image of FIG. 6(E). From these results, it was confirmed that Cy5 dissociated from the Micelle-PC-Latex-1 as a result of light irradiation is incorporated into the cell.

The Micelle-PC-Latex-1 in the above-described Examples 1 to 3 is a model of a medical instrument (balloon) comprising a polymeric micelle on which Cy5 used as a model reagent is loaded. The results of the above-described Examples 1 to 3 show the following findings.

(i) A polymeric micelle that was a drug (Cy5)-loaded nanostructure could be immobilized, via a covalent bond, on the surface of a latex bead used as a medical instrument model, mediated by a photosensitive linker.

(ii) As a result of the photocleavage of the photosensitive linker due to light irradiation, the polymeric micelle as a nanostructure was dissociated, and the drug (Cy5) could be released from the surface of the latex bead.

(iii) It was confirmed that the drug (Cy5) released due to the cleavage by light irradiation was incorporated into the cell.

From the aforementioned results, it was confirmed that it is possible to deliver a drug-loaded nanostructure immobilized on the surface of the medical instrument to a target site, and to photocleave a photosensitive linker in the target site, thereby releasing the nanostructure and the drug. The type of the reagent to be loaded, a loading method, the type of the nanostructure, the type of the bond between the nanostructure and the medical instrument, the type of the photosensitive linker, and the like can be appropriately changed by those skilled in the art according to ordinary methods, and the present method can be applied to various nanostructures, drugs, and medical instruments.

INDUSTRIAL APPLICABILITY

According to the present invention, there can be provided a medical instrument, which is capable of delivering a drug to a target site in a state in which the drug is loaded on a nanostructure, and is also capable of releasing the nanostructure and/or the drug loaded on the nanostructure by being exposed to a light in the target site. The medical instrument of the present invention enables efficient transportation of a drug to a target site and also enables a controlled release of the drug in the target site, and thus, the present medical instrument is excellent in terms of practicality and usefulness.

It is to be noted that all documents and publications cited in the present description are incorporated herein by reference in their entireties, regardless of the purpose thereof. In addition, the present description includes the contents as disclosed in the claims, description, and drawings of U.S. Provisional Application No. 62/872,911 (filed on Jul. 11, 2019), which is a priority document of the present application.

REFERENCE SIGNS LIST

1, 26 Medical instrument (balloon)
11 Nanostructure
12, 32 Photosensitive linker
12*a*, 32*a* Photosensitive portion
13 Surface of medical instrument (balloon)
21 Polymeric micelle
22 Block copolymer
24 Drug
25 Functional group
33 Medical instrument (latex bead)
hν Light

The invention claimed is:

1. A medical instrument that is inserted into an affected area or tissue to perform treatment, wherein a drug-loaded nanostructure is covalently bound to the medical instrument via a photosensitive linker immobilized on the surface of at least a portion of the medical instrument;

the photosensitive linker has a first functional group that forms a covalent bond with a terminal functional group on the surface of the nanostructure, the nanostructure is a polymeric micelle, and the polymeric micelle is configured to comprise a block copolymer comprising a hydrophilic polymer chain and a polymer chain and the polymeric micelle has a core-shell structure having a core portion comprising the polymer chain and a drug and a shell portion comprising the hydrophilic polymer chain.

2. The medical instrument according to claim 1, wherein the size of the nanostructure is 20 nm to 500 nm.

3. The medical instrument according to claim 1, wherein the drug comprises at least one selected from among an agent, a pharmaceutical product, a diagnostic drug, and a nutritional supplement.

4. The medical instrument according to claim 1, wherein the drug is enclosed in the nanostructure, or is physically or chemically bound to the nanostructure.

5. The medical instrument according to claim 1, wherein the drug is soluble in water.

6. The medical instrument according to claim 1, wherein the photosensitive linker is cleaved or decomposed by being exposed to a light, so that the nanostructure is released.

7. The medical instrument according to claim 6, comprising two or more types of photosensitive linkers that are cleaved or decomposed with lights each having different wavelengths.

8. The medical instrument according to claim 1, wherein the photosensitive linker comprises at least one selected from among a double bond that binds two carbon atoms to each other, an azo bond, a peroxide bond, a bond that binds a carbon atom to a nitrogen atom, and a structure represented by the following formula (I):

(I)

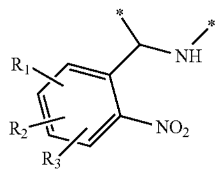

wherein * represents a binding site, and $R_1$, $R_2$, and $R_3$ each independently represent a hydrogen atom, lower alkyl, lower alkoxy, amino, a halogen atom, hydroxy or cyano, or any two of the adjacent $R_1$, $R_2$, and $R_3$ together form a methylenedioxy group.

9. The medical instrument according to claim 1, which is for use in the delivery of the drug to a tissue.

10. The medical instrument according to claim 1, wherein the tissue comprises at least one selected from among coronary vascular system, peripheral vascular system, cerebrovascular system, esophagus, airway, sinus, trachea, colon, bile duct, urinary tract, prostate, intracerebral duct, and lower limbs.

11. The medical instrument according to claim 1, which is selected from among a balloon, a catheter, a stent, and a probe.

12. The medical instrument according to claim 1, further comprising a light source for use in the exposure of the photosensitive linker to a light, wherein the light source is selected from a light-emitting diode and a semiconductor laser.

13. The medical instrument according to claim 1, further comprising a secondary medical instrument having an optical fiber or a photonic crystal fiber for use in the exposure of the photosensitive linker to a light.

14. The medical instrument according to claim 1, wherein the photosensitive linker is cleaved or decomposed by being exposed to a light in a region at a wavelength of 200 to 1000 nm.

15. The medical instrument according to claim 1, wherein the drug is insoluble in water.

16. The medical instrument according to claim 1, wherein a combination of the first functional group and the terminal functional group on the surface of the nanostructure is selected from: a dibenzocyclooctyne (DBCO) group and an azide group, a carboxyl group and an amino group, and a thiol group and a maleimide group.

* * * * *